ically Modified (Hydroxyethyl) Cellulose", ACS Adv. in Chem. Series, pp. 101–110, (1986).

Primary Examiner—Judy M. Reddick
Assistant Examiner—J. M. Reddick
Attorney, Agent, or Firm—Mark L. Rodgers; William F. Marsh; James C. Simmons

United States Patent [19]
McAndrew et al.

[11] Patent Number: 5,270,379
[45] Date of Patent: Dec. 14, 1993

[54] AMINE FUNCTIONAL POLYMERS AS THICKENING AGENTS

[75] Inventors: Thomas P. McAndrew, Macungie; Andrew F. Nordquist, Whitehall; Robert K. Pinschmidt, Jr.; Donald P. Eichelberger, both of Allentown, all of Pa.

[73] Assignee: Air Products and Chemcials, Inc., Allentown, Pa.

[21] Appl. No.: 938,930

[22] Filed: Aug. 31, 1992

[51] Int. Cl.$^5$ .................... C08L 29/04; C08L 39/02
[52] U.S. Cl. .................... 524/555; 524/557; 525/60; 526/307.1
[58] Field of Search ........... 524/555, 557; 525/60; 526/307.1

[56] References Cited

U.S. PATENT DOCUMENTS

| | | | |
|---|---|---|---|
| 3,779,970 | 12/1973 | Evani et al. | 260/29.6 |
| 4,079,028 | 3/1978 | Emmons et al. | 260/29.6 |
| 4,228,277 | 10/1980 | Landoll | 536/90 |
| 4,393,174 | 7/1983 | Dawson et al. | 525/328.2 X |
| 4,421,602 | 12/1983 | Brunnmueller et al. | 525/328.2 X |
| 4,426,485 | 1/1984 | Hoy et al. | 524/591 |
| 4,490,557 | 12/1984 | Dawson et al. | 525/351 X |
| 4,507,426 | 3/1985 | Blake, Jr. | 524/505 |
| 4,551,513 | 11/1985 | Engelhardt et al. | 524/555 X |
| 4,735,981 | 4/1988 | Rich et al. | 524/247 |
| 4,774,285 | 9/1988 | Pfohl et al. | 525/328.2 X |
| 4,843,118 | 6/1989 | Lai et al. | 524/555 |
| 4,921,621 | 5/1990 | Costello et al. | 524/555 X |
| 5,086,111 | 2/1992 | Pinschmidt, Jr. et al. | 525/61 |

OTHER PUBLICATIONS

R. A. Gelman et al, "Viscosity Studies of Hydrophobi-

[57] ABSTRACT

Fluid coating materials such as paints, ink pastes, personal care creams and the like having a water-base are thickened with an associative thickener which is a vinylamine polymer having a weight average molecular weight above $10^5$ and which has been modified by reaction with at least 0.2 mer percent of a linear monoaldehyde having 8 to 30 carbon atoms. A hydrolyzed polymer of N-vinylformamide which has been hydrophobically modified with an aldehyde such as dodecaldehyde, exhibits associative thickening characteristics and is useful in thickening water-based formulations.

6 Claims, 3 Drawing Sheets

5,270,379

AMINE FUNCTIONAL POLYMERS AS THICKENING AGENTS

FIELD OF THE INVENTION

This invention relates to fluid formulations thickened with hydrophobically-modified amine functional polymers. In another aspect it relates to a method of thickening fluid compositions with hydrophobicallymodified amine functional polymers.

BACKGROUND OF THE INVENTION

Associative thickeners are hydrophobically-modified water soluble polymers that offer improved rheological performance over traditional thickeners. They represent a relatively new technology in the field of water-soluble polymers and have received considerable attention, particularly over the last decade. The molecular structure requirements necessary to induce association have been discussed in the literature with respect to a variety of synthetic polymers.

Thickeners, in general are natural or synthetic polymers used to modify the viscosity characteristics of fluids. While they are most often used as components of water-based systems, such as in latex paints, they can sometimes be used in nonaqueous systems. The most prominent category of thickening agents is cellulosic polymers, such as carboxymethyl cellulose (CMC) and hydroxyethyl cellulose (HEC).

In the early 1980s, a new type of synthetic thickener, called an associative thickener, was developed. The object was to improve some of the performance deficiencies of cellulosic thickeners in latex paints. Associative thickeners are water-soluble polymers that have been modified by the addition of controlled amounts of certain hydrophobic groups. In solution, these hydrophobic groups are believed to associate with each other and also, in some cases, with pigment and latex components that are present in paint and other coating-type formulations. Such inter-molecular associations are believed to account for a thickening action which cannot be explained by the molecular weight of the thickening agent.

U.S. Pat. No. 4,228,277, Landoll (1980) discloses modifying cellulose ethers, such as hydroxyethyl cellulose, with long chain alkyl groups having 10 to 24 carbon atoms, in order to improve the viscosifying effect of the cellulose ethers. Modification is by reaction with long chain epoxides or halides. See also Gelman, et al., "Viscosity Studies of Hydrophobically Modified (Hydroxyethyl) Cellulose", ACS Adv. in Chem. Series, pages 101-110 (1986) for a discussion of associative thickening with hydrophobically modified hydroxyethyl cellulose.

Synthetic compositions based upon vinylpolymers had been prepared much earlier and these compositions may have operated in the same manner as associative thickeners.

U.S. Pat. No. 3,779,970, Evani, et al., (1973) discloses thickening latex coatings such as paints with an ester of a carboxylic polymer in which some of the pendent carboxylic acid groups have been esterified with a nonionic surfactant, such as nonyl phenol, condensed with excess ethylene oxide to form a hydrophobic group spaced from the polymer backbone with a hydrophilic polyethylene oxide. The paint is said to have improved flow and leveling properties. Vinyl acetate can be copolymerized to prepare the carboxylic polymer.

More recently, attention in this field appears to have been directed toward modified urethane polymers. U.S. Pat. No. 4,079,028, Emmons, et al., (1978) discloses thickening aqueous systems, such as water-based paints, with a low molecular weight polyurethane having at least three hydrophobic groups connected by hydrophilic polyether groups. The molecular weights of these polymers are said to range from 10,000 to 200,000, preferably 12,000 to 150,000. Polymers are made in nonaqueous media involving polyether polyels and isocyanates. It is said that these products are potentially useful in the manufacture of paints, textile coatings, printing inks, herbicides, topical medicines, cosmetics and hair conditioners.

U.S. Pat. No. 4,426,485, Hoy, et al., (1984) describes what is represented as an improvement over the '028 polymer thickeners in the development of polymers having hydrophobic segments "bunched" together rather than distributed along the polymer chain. Polymers exemplified include condensation polymers of polyethylene glycol and toluenediisocyanate which are reacted with a hydrophobic diol.

Another approach which has been made to obtain improvements over the '028 thickeners has been to develop blends of polymers. U.S. Pat. No. 4,507,426, Blake (1985) describes thickening agents for paints made by blending urethane polymers as described by the '028 patent with an alkali-soluble aqueous emulsion polymer made from a carboxylic acid monomer, such as acrylic acid, a nonionic vinyl monomer, such as alkyl esters of acrylic acid, and a nonionic vinyl surfactant ester, such as alkylphenoxypoly(ethyleneoxy) ethylacrylates.

U.S. Pat. No. 4,735,981, Rich, et al., (1988) describes still another improvement on the blended thickeners of the '426 patent in which a nonionic urethane monomer is used instead of the nonionic vinyl surfactant ester.

A new class of polymers known as hydrophobically modified amine functional polymers is described by U.S. Pat. No. 5,086,111, Pinschmidt, et al., (1992). This patent discloses monoaldehyde modified poly(vinylamine) which can be a homopolymer or a copolymer with polyvinyl alcohol. The use of aldehyde modifiers containing as high as 21 carbon atoms is disclosed, but the discussion centers around monoaldehydes containing from 1 to 7 carbon atoms. The products are said to be useful as flocculants, in emulsifiers and as protective colloids, and also as epoxy resin and polyurethane crosslinking agents. The molecular weights of these polymers range from 10,000 to $7 \times 10^6$ and flocculation of bentonite aqueous suspension is demonstrated.

Copending patent application Ser. No. 07/803,256 filed Dec. 5, 1991 and now U.S. Pat. No. 5,185,083 describes using the same polymers of the '111 patent in wastewater treating in order to assist in separating the solids from aqueous suspensions. Other utilities disclosed include crosslinking polymers, use in emulsifiers and as protective colloids. Aldehyde modifiers containing 2 to 8 carbon atoms are specifically named. In copending application Ser. No. 07/826,330 filed Jan. 24, 1992 and now U.S. Pat. No. 5,232,553 polymers as described by the '111 patent, particularly modified with aldehydes having 2 to 12 carbon atoms, are described as useful in papermaking to retain fines, especially in recycle waste. A waste paper pulp slurry is described treated with a $C_{12}$-modified polyvinyl amine hydrochloride having a molecular weight of $6.4 \times 10^5$ and it is shown that the polyvinyl amine modified with a $C_4$ aldehyde provides better performance in this particular service than the $C_{12}$-modified polymer.

SUMMARY OF THE INVENTION

We have discovered that certain hydrophobically modified amine functional polymers can function as associative thickeners and thereby find unexpected utility in particular applications. According to our invention, a water-based fluid coating material is provided containing a thickening amount of a polyvinyl amine polymer which has a weight average molecular weight above $10^5$ and has been modified by reaction with at least 0.2 mer percent of a linear monoaldehyde having 8 to 30 carbon atoms. The expression "mer percent" designates the mole proportion of the modifier based upon the monomer units which have gone into making the vinylamine polymer. For example, a preferred form of this polymer is made by homopolymerizing N-vinylformamide which is then hydrolyzed to convert the amide groups to amine groups, thereby forming the poly(vinylamine). Such a polymer can be hydrophobically modified to be useful in our invention by reaction with at least 0.2 moles of the linear monoaldehyde per 100 moles of the vinylamine groups present on the polymer.

Also according to our invention, a water-based formulation is thickened by incorporating into the formulation a vinylamine polymer having a weight average molecular weight of $2 \times 10^5$ to $2 \times 10^6$ modified by reaction with at least 0.2 mer percent linear monoaldehyde having 8 to 30 carbon atoms.

DETAILED DESCRIPTION OF THE INVENTION

Figure 1:
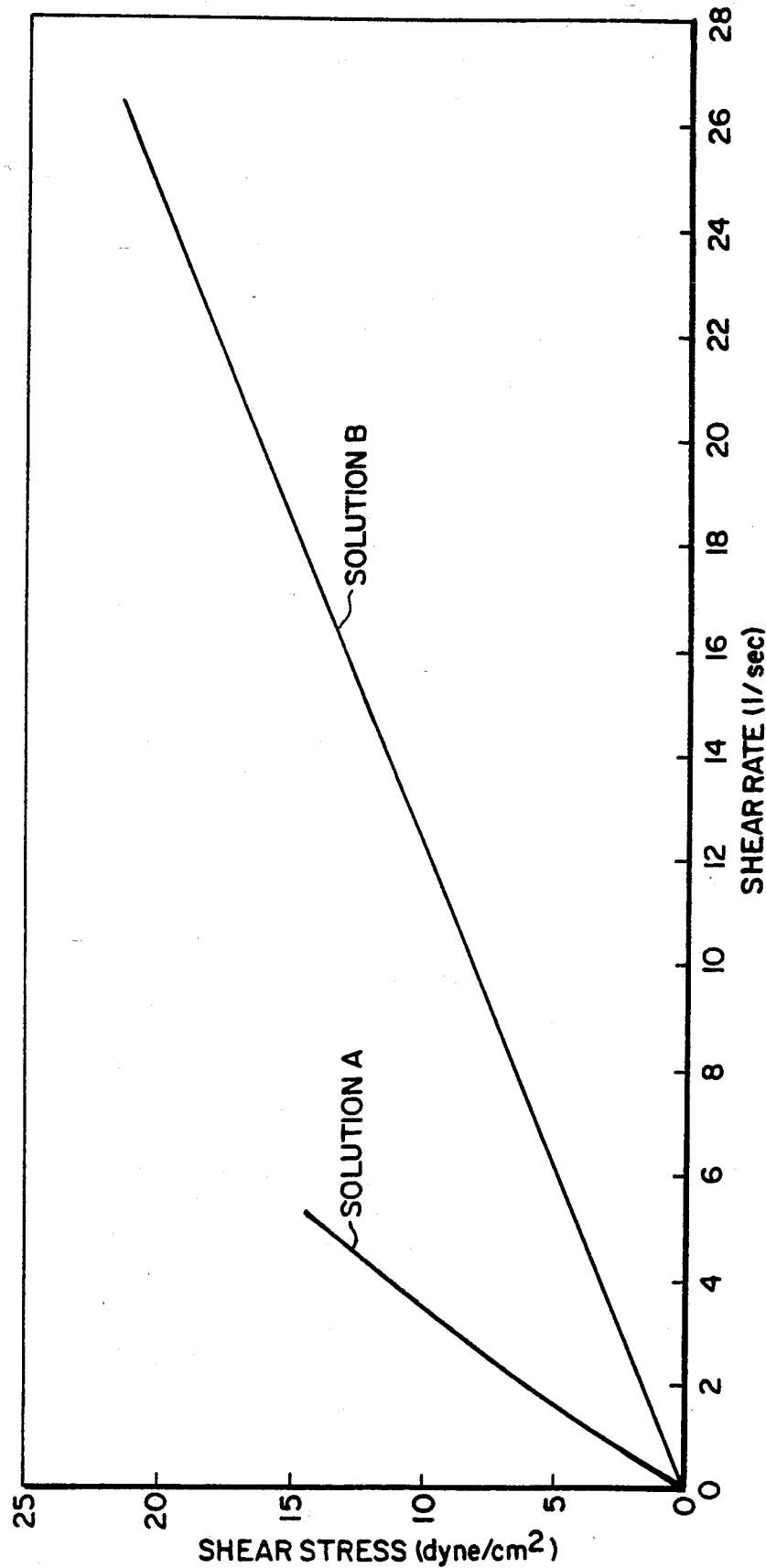
FIG. 1 is a plot of shear stress versus shear rate for solution A containing the hydrophobically-modified poly(vinylamine).HCl according to the invention compared to a similar plot for solution B which contains the unmodified poly(vinylamine) hydrochloride at the exact same concentration (wt %).

The polymers which can be used as associative thickeners according to our invention are the amine functional polymers containing acetal groups prepared as described in U.S. Pat. No. 5,086,111, but limited to those polymers which have a weight average molecular weight above $10^5$ and preferably the molecular weight is in the range of $2 \times 10^5$ to $2 \times 10^6$. The aldehyde modification must be carried out to the extent that the reaction incorporates at least 0.2 mole percent of the aldehyde which must in turn hove 8 to 30 carbon atoms and be linear, for example n-octylaldehyde, n-decylaldehyde, dodecaldehyde, octadecyldehyde, and the like. Preferably, the modified vinylamine polymer contains 0.5 to 20 moles of incorporated monoaldehyde per 100 moles of polymerized monomer units.

The polymers are formed first by polymerization of N-vinylamide, such as N-vinylformamide (NVF) or N-vinylacetamide, and the like, followed by a hydrolysis to convert the pendent amide groups to amine groups. Hydrolysis can be partial or complete, but it is preferred to proceed with the hydrolysis to substantial completion which would be approximately 90 to 95% conversion of the amide groups to amine units. Following hydrolysis, hydrophobic modification is achieved by reaction with an appropriate aldehyde at a level designed to give the desired substitution. The N-vinylamide can be copolymerized with a vinyl ester such as vinyl acetate which on hydrolysis converts to vinyl alcohol. Homopolymers of N-vinylamides such as NVF are preferred.

The materials which are thickened according to our invention are fluid coating materials which include a broad variety of products having the common feature that they must have sufficient body to be applied to a surface and be retained on that surface, while also being sufficiently fluid to form a smooth, coherent film which, in effect, forms a new surface on the old. The most common coating material of this nature is a waterbased latex paint, but it is intended that these coating materials include such diverse products as personal care formulations such as emollients, and hair conditioning shampoos, pigmented printing inks, paper and textile coatings, and topical medicines.

Since a major application of associative thickeners is in paints, a brief discussion of paint rheology is useful. A successful paint formulation must satisfy several demanding, and often contradictory, requirements. Many of these requirements are related to the rheological characteristics of the paint.

Paint experiences a very high shear rate, up to 10,000 reciprocal seconds (l/s), at the moment of application. For ease of application and spreading, the viscosity should be relatively low under these high shear conditions. However, sufficient viscosity must be maintained to prevent overspreading, which can lead to poor hiding. Immediately after application, the paint returns to a low shear environment, around 0.01 to 0.1 l/s, where again the viscosity characteristics need to be effectively controlled. The paint should undergo a small amount of flow to provide for leveling of brush marks, or applicator patterns, and formation of a smooth surface. However, if flow is too great, sags and drips can form, detracting from the final appearance.

Oil-based alkyd paints are generally considered to have the most desirable combination of rheological characteristics. However, they fall short on consumer acceptability because of odor problems and difficulty in clean-up. For this reason, water-based latex paints have come to dominate the architectural paint market, and now account for more than 75% of trade paint sales. Latex paint application characteristics are acceptable, but fall short of the performance provided by oil-based alkyds. Thus, there is continued interest in additives (such as associative thickeners) that would improve application.

Hydroxyethylcellulose (HEC), the most widely used thickener for latex paints, suffers from several drawbacks. It is subject to enzyme and microbial attack, leading to degradation of the polymer backbone. This destroys thickening performance. HEC provides relatively good low shear performance, but is subject to breakdown under high shear conditions. This can lead to overspreading and poor hiding performance. Viscosity recovery after shearing is very rapid and can result in poor leveling and excessive brush marks. Conversely, sag resistance is good. HEC also exhibits a tendency toward haze formation and has poor scrub resistance and unfavorable interactions with some pigments which can lead to poor color control.

In spite of these problems, HEC generally provides adequate performance for flat interior latex paints, which is the largest volume architectural paint category. The performance deficiencies are most noticeable in semi-gloss and high gloss interior paints, and in exterior paints. It is in these areas where associative thickeners have made their greatest contributions.

Conventional thickeners, such as HEC, are believed to provide viscosity enhancement by two mechanisms, solvent immobilization (swelling) and chain entanglement. Associative thickeners add a third performance element, hydrophobic association. The basic concept of an associative thickener is to incorporate a small number of hydrophobic groups spaced along the backbone of a normally water-soluble polymer. The weak intermolecular association of these groups provides an apparent increase in molecular weight of the polymer and thus improves thickening performance, especially under low shear conditions. Additionally, in paints, the groups may associate with latex particles or pigment particles (particle bridging), leading to network formation and increased resistance to flow. The associative thickeners of the present invention can be added to any typical water-based paint formulation, typically from about 0.1 to 5 wt % based on the total formulation, although the optimum amount of thickener will depend upon the specific formulation and type of paint.

The associative thickeners of this invention are prepared by reaction of an aldehyde with a poly(-vinylamine)-HCl or a copolymer of poly(vinylamine/-vinyl alcohol).HCl. These polyvinylamines must have a molecular weight greater than $10^5$, preferably in the range of $2\times10^5$ to $2\times10^6$ and more preferably from $5\times10^5$ to $1\times10^6$ weight average molecular weight. Methods for preparing such polymers are well known in the literature.

The poly(vinylamine) or the copolymer can be used either as a salt, for example the hydrochloride or as a free amine and is dissolved in water at a concentration which produces a stirrable solution for modification with the monoaldehyde. Such solutions normally range from 0.5 to 80 wt. % but preferably are 10 to 50 wt. %. A suitable method for modification involves preparing a suspension of the polymer, acidifying poly(vinylamine) in a medium which is a nonsolvent for the polymer, but a solvent for the aldehyde. Alcohols, such as methanol, ethanol, propanol, isopropanol, butanol, t-butanol, isobutanol, or 3-methoxy-2-propanol, or ethers, such as diethyl ether, t-butyl methyl ether, and glymes are suitable as the reactive medium. Alternatively, an aqueous solution or suspension can be prepared using isolated amine-containing polymer, or without isolating the polymer, simply by hydrolyzing poly(N-vinylformamide) or an NVF copolymer and performing the reaction in the hydrolyzate mixture. For example, NVF can be polymerized in water, hydrolyzed to the polyvinylamine and modified with an aldehyde without isolation of intermediates. Alternatively hydrolysis of NVF (co)-polymer as a suspension in a nonsolvent, e.g. a lower alcohol, allows removal of byproduct sodium formate by precipitation. Careful acidification of such a mixture after sodium formate separation can produce a suspension of polyvinylamine acid salt which is useful for modification to the products employed in our invention.

For modification with the aldehyde, the pH of the amine containing polymer mixture is adjusted to 5 or below, preferably 1 to 3, with a mineral acid, such as hydrochloric, sulfuric, or perchloric acid, or with an organic acid such as formic, trifluoroacetic, methane sulfonic, or an aryl sulfonic acid. If the solution is prepared from polyvinylamine hydrochloride, the pH does not need adjusting.

Suitable modifying monoaldehydes are branched or preferably linear aliphatic aldehydes containing 8 to 30 and preferably 10 to 20 carbon atoms. By "linear" it is meant that there is preferably no branching and at most minimal branching of not more than 2 methyl groups.

The level of aldehyde substitution must be greater than 0.1 mer percent, and is preferably 0.5 to 20 mer percent in order to be effective in our invention. The optimum aldehyde substitution varies with aldehyde length. With $C_{12}$ or larger aldehydes, 0.2 to 5 mol percent are preferred. Lower aldehydes work best at higher percent modification. The modification reaction can be carried out between 0° C. and 100° C., but is preferably in the range of 20° to 60° C. Thoroughly mixing the reagents at lower temperature minimizes the difficulty of mixing a reaction which is extremely viscous because of the formation of the associative thickener. The final product can be used as a solution or suspension or can be isolated from the mixture prior to incorporation into the coating compositions according to the invention. It is believed that the best modification of the polyvinylamine hydrochloride to prepare an associative thickener would be with about 1 mer percent of an aldehyde having a chain length of 10 or more carbon atoms.

In order to describe our invention further, the following examples are presented which are illustrative only and should not be construed to limit unduly the scope of the invention.

EXAMPLE 1

A one liter reactor was charged with 120.1 g (1.69 moles) of N-vinylformamide (NVF), 480 mL of deionized water, and 0.834 g (0.00308 moles) of Mixxim I-100 [2,2'azobis(amidinopropane hydrochloride)]. The solution was sparged with nitrogen while stirring at 200 RPM and 20° C. for 75 minutes. The nitrogen purge was stopped and a nitrogen blanket maintained as the reaction was heated to 55° C. over 20 minutes. The reactor was held at 55° C. for 5.25 hr and then cooled to room temperature.

The thus formed poly(N-vinylformamide) was hydrolyzed to polyvinylamine by adding 140 g (1.75 moles) of 50 wt %, sodium hydroxide and 100 mL of water to the reaction mix. The reaction was heated to 80° C. over 55 minutes and held at 80° C. for 8 hours. After cooling to room temperature, 422 mL (5.06 moles) of concentrated hydrochloric acid was added to the reaction mix, precipitating poly(vinylamine) hydrochloride. After decanting the light layer, the precipitated polymer was soaked in 500 mL of isopropanol for 8 hours to remove water. After repeating the soak three times, the toughened polymer was ground to 40 mesh, soaked in isopropanol again, and vacuum dried at 65° C. The recovered 126.9 g of product had a weight average molecular weight (Mw) of 510,000 and a number average molecular weight (Mn) of 143,000.

EXAMPLE 2

A round bottom flask equipped with a water cooled condenser and a mechanical stirrer was charged with a solution containing 600.0 g (8.44 moles) of N-vinylformamide, 2,400 g of deionized water, and 4.170 g (0.01688 moles) of Mixxim I-100 [2,2′ azobis(amidinopropane hydrochloride)]. The solution was sparged with nitrogen while stirring at approximately 200 RPM and 20° C. for 75 minutes. The nitrogen purge was stopped and a nitrogen blanket maintained as the reaction was heated to 55° C. over 20 minutes. The reactor was held at 55° C. for 5 hr. and then cooled to room temperature.

After heating the reaction mix to 80° C., the poly(N-vinylformamide) was hydrolyzed to polyvinylamine by adding a solution containing 337.60 g (8.44 moles) of sodium hydroxide dissolved in 400 g of water over 0.5 hours. The reaction was held at 80° C. for 9 hours. After cooling to room temperature, 2,100 mL (25.2 moles) of concentrated hydrochloric acid was added to the reaction mix, precipitating polyvinylamine hydrochloride. The light layer was decanted, and the precipitated polymer was soaked in 1,000 mL of isopropanol for 4 hours to remove water, followed by another soak in 2 L of isopropanol, and a 16 hour soak in 1,000 ml of methanol. The toughened polymer was air dried, ground to 40 mesh, and vacuum dried at 60° C. and 1 torr. The recovered 639.1 g of product had $M_n = 145,000$ and $M_w = 642,000$.

EXAMPLE 3

Preparation of Dodecaldehyde Modified Poly(vinylamine)

A round bottom flask equipped with an overhead stirrer and a water cooled condenser was charged with 107.6 of a 10 wt % aqueous solution of the PVAm.HCl of Example 2. After heating the reactor to 65° C., a solution containing 0.1953 g of 96% pure dodecaldehyde and 10 mL of isopropanol was added over 5 minutes. After another 5 minutes the reaction mix thickened. Twenty minutes after the start of addition, the reaction was cooled. The polymer air dried to a brittle yellow film which was then soaked in 200 mL of isopropanol to extract unreacted dodecaldehyde and dried at 50° C. and 5 torr for 16 hours. The product contained 0.75 mole percent dodecaldehyde based on the vinylamine monomer units in the polymer.

EXAMPLE 4

Preparation of 5% Dodecaldehyde Modified Poly(vinylamine)

A round bottom flask equipped with an overhead stirrer and a water cooled condenser was charged with 100.0 g of a 10 wt % aqueous solution of the PVAm.HCl of Example 2. The reactor was cooled to 0° C. and a solution containing 10 g of isopropanol and 1.226 g of dodecaldehyde was added to the reaction with rapid mixing. The resulting emulsion was heated to 65° C. over 50 minutes and held at temperature for 20 minutes resulting in a gel. The gel was soaked in isopropanol, ground to approximately 40 mesh, vacuum dried at 40° C., Soxhlet extracted for 15 hours with isopropanol, and vacuum dried again.

EXAMPLE 5

Aqueous solutions were prepared containing 1.25 weight percent of the product of Example 3 (Solution A) and 1.25 weight percent of the unmodified PVAm.HCl of Example 2 (Solution B). Brookfield viscosities (Cylindrical spindle No. 1) were run on both solutions. Viscosity of Solution A was 275 cps while that of Solution B was only 82 cps. Shear stress (dyne/cm$^2$) was plotted against shear rate (reciprocal seconds) and the results are shown in FIG. 1.

There is a slight curvature to the plot for Solution A, indicating non-Newtonian behavior, or in other words, slight shear thinning. These results demonstrate associative thickening by the modified polymer of Example 3. The increase in viscosity for Solution A of over three fold compared to Solution B cannot be attributed to the modest increase in molecular weight owing to the dodecaldehyde addition. Associative bonding between the hydrophobic extensions of the modified molecules is consistent with the observed thickening and shear thinning as shear rate increased.

EXAMPLE 6

Comparative

In a round bottom flask, 80 g (0.725 mol es) of PVAm.HCl containing approximately 28 wt % sodium chloride and having Mw of approximately 100,000 was dissolved in 320 mL of deionized water. The reaction was heated to 40° C. and a solution of 1.39 g (0.00733 moles) of 96% dodecaldehyde dissolved in 10 mL of isopropanol was added over 3 minutes. The reaction was heated to 65° C. over 5 minutes, and held at temperature for 30 minutes. After cooling to room temperature, the modified polymer was precipitated by the addition of 120 mL (1.44 moles) of concentrated hydrochloric acid. After decanting the light layer, the precipitated polymer was soaked in 500 mL of isopropanol for 8 hours to remove water. After repeating the soak, the toughened polymer was ground to 20 mesh, soaked in isopropanol again, and vacuum dried at 65° C. The recovered 42.5 g of product contained about 1 mole percent dodecaldehyde and had Mw=128,000 and Mn=61,800. Aqueous solutions of this product were not significantly more viscous than solutions of the unmodified PVAm.HCl. This shows that, to achieve associative thickening, the unmodified PVAm.HCl should have a Mw greater than $10^5$.

EXAMPLE 7

Comparative

Benzaldehyde Modified Poly(vinylamine) was prepared by charging a round bottom flask equipped with an overhead stirrer and a water cooled condenser with 127.04 g of a 9.91 wt %, pH 2.0, solution of the PVAm.HCl prepared in Example 2 above. (The solution contained 0.158 moles of PVAm.HCl). After heating the flask to 65° C. and while stirring at 300 RPM, a solution containing 6.27 g (0.0592 moles) of benzaldehyde and 6 mL of isopropanol was added over seven minutes, producing an emulsion. After 90 minutes at 65° C., the emulsion was cooled to room temperature and 76.5 g was poured into 400 mL of isopropanol. The precipitated polymer was washed twice, once for 16 hours, and once for 3 hours, each time in 130 mL of isopropanol, to remove water. After drying at 65° C. and 250 torr, 7.59 g of polymer, substituted with 3.2 mer % benzylidene, having molecular weights of Mn=144,000 and Mw=593,000, and containing approximately 23% residual isopropanol, was recovered.

Figure 2:
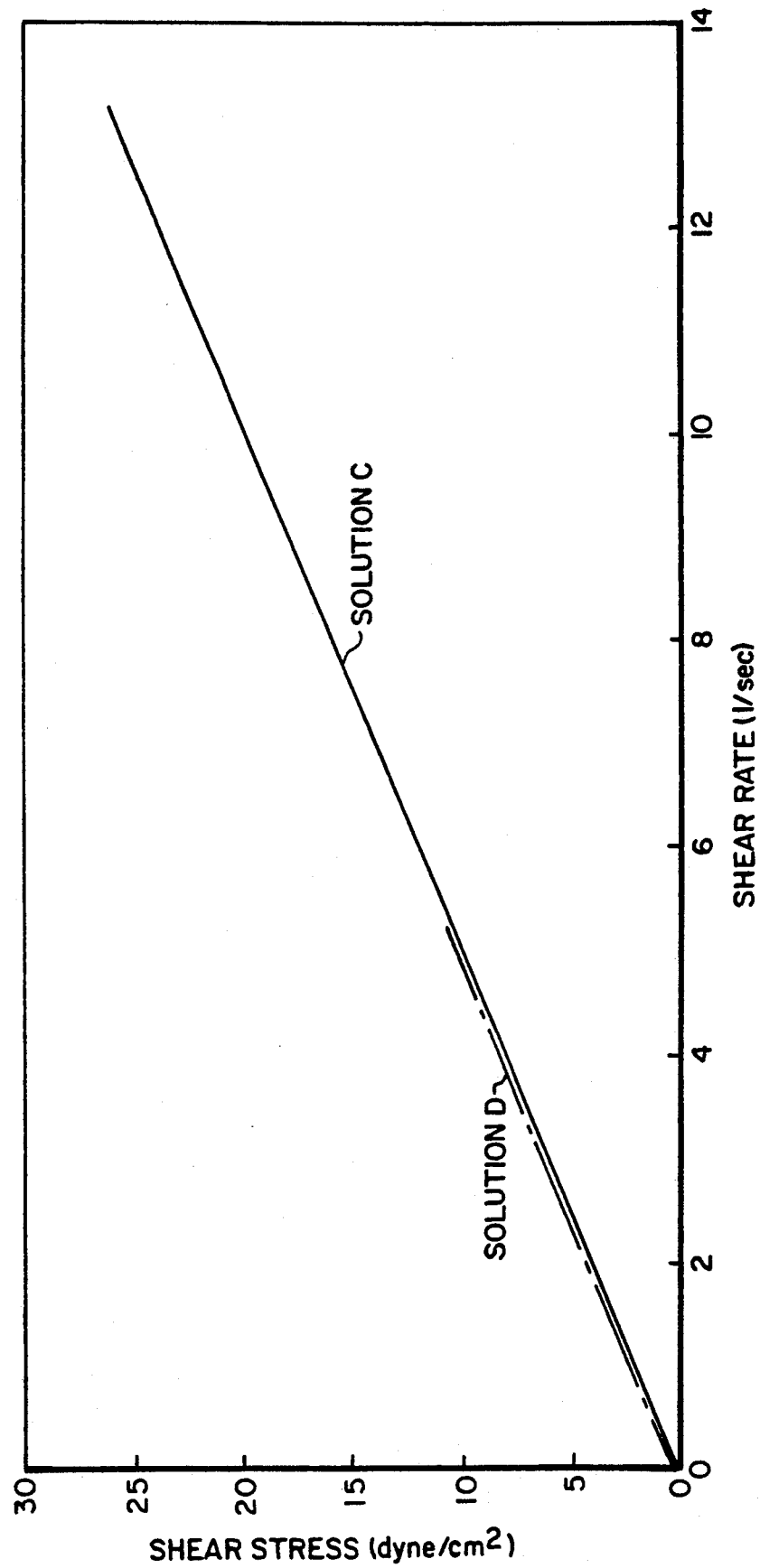
FIG. 2 is a plot of viscosity data similar to FIG. 1, presented for comparison purposes, and showing solutions thickened with a poly(vinylamine) hydrochloride polymer and with the same polymer modified with a shorter chain monoaldehyde.

Solutions C and D were prepared from the benzaldehyde modified and unmodified polymers, respectively, at 3.0 weight percent in water. The Brookfield viscosities of the two solutions were virtually identical, 197 cps for Solution C and 204 cps for Solution D. Plots of shear stress versus shear rate are shown in FIG. 2. No associative thickening is evidenced, indicating that the hydrophobic aldehyde modifier should have more than 7 carbon atoms. These data also show that the increase in molecular weight of the PVAm-HCl brought about by the aldehyde additions cannot explain the thickening effects observed for Example 5.

EXAMPLE 8

Comparative

High molecular weight PVAm.HCl was prepared by charging a round bottom flask equipped with a water cooled condenser and a mechanical stirrer with a solution containing 250 g (3.52 moles) of polyNVF and 9750 g of deionized water. While stirring, 282 g of 50% aqueous sodium hydroxide was added rapidly, and the flask was heated to 80° C. After heating for an additional 10 hours and cooling to room temperature, the polymer was precipitated by addition of approximately 2 L of concentrated hydrochloric acid. After decanting the liquid, the precipitated PVAm.HCl was dissolved in enough water to produce a fluid solution, and the solution was slowly added to vigorously stirred methanol, re-precipitating the polymer. The precipitate was washed with methanol and dried at 60° C. in vacuo., producing 141 g of PVAm.HCl, having $Mn=463,000$ and $Mw=1,510,000$.

The resulting high molecular weight poly(vinylamine) hydrochloride was then modified with 18 mol percent butyraldehyde so that the product had 18 n-$C_4H_8$ groups per 100 monomer (vinylamine) units along the polymer chain. The butyraldehyde modification was carried out by charging a 2 L resin kettle equipped with a stirrer and a water cooled condenser with a solution containing 40.02 g (0.503 moles) of the high molecular weight polyvinylanline.HCl and 640 g of deionized water. While stirring the kettle at approximately 100 RPM at room temperature, a solution containing 40.3 g of methanol, 18.12 g (0.252 moles) of butyraldehyde, and 2.09 (0.020 moles) of concentrated sulfuric acid was added. A local precipitate formed when the solution was added, but after heating the kettle to 65° C. and holding at 65° C. for another 1.5 hours, the precipitate dissolved. After cooling to room temperature, the contents of the reactor were added to 3 L of acetone, precipitating the polymer. The precipitate was washed three times, twice for 16 hours and once for 7 hours, each time in approximately 500 mL of acetone to remove water. After dicing and drying at 40° C. and 5 torr for 3 days, 42.13 g of polymer, substituted with 18.2 mer % butylidene, having molecular weights of $Mn=593,000$ and $Mw=1.542,000$, and containing approximately 17% residual isopropanol, was recovered.

Figure 3:
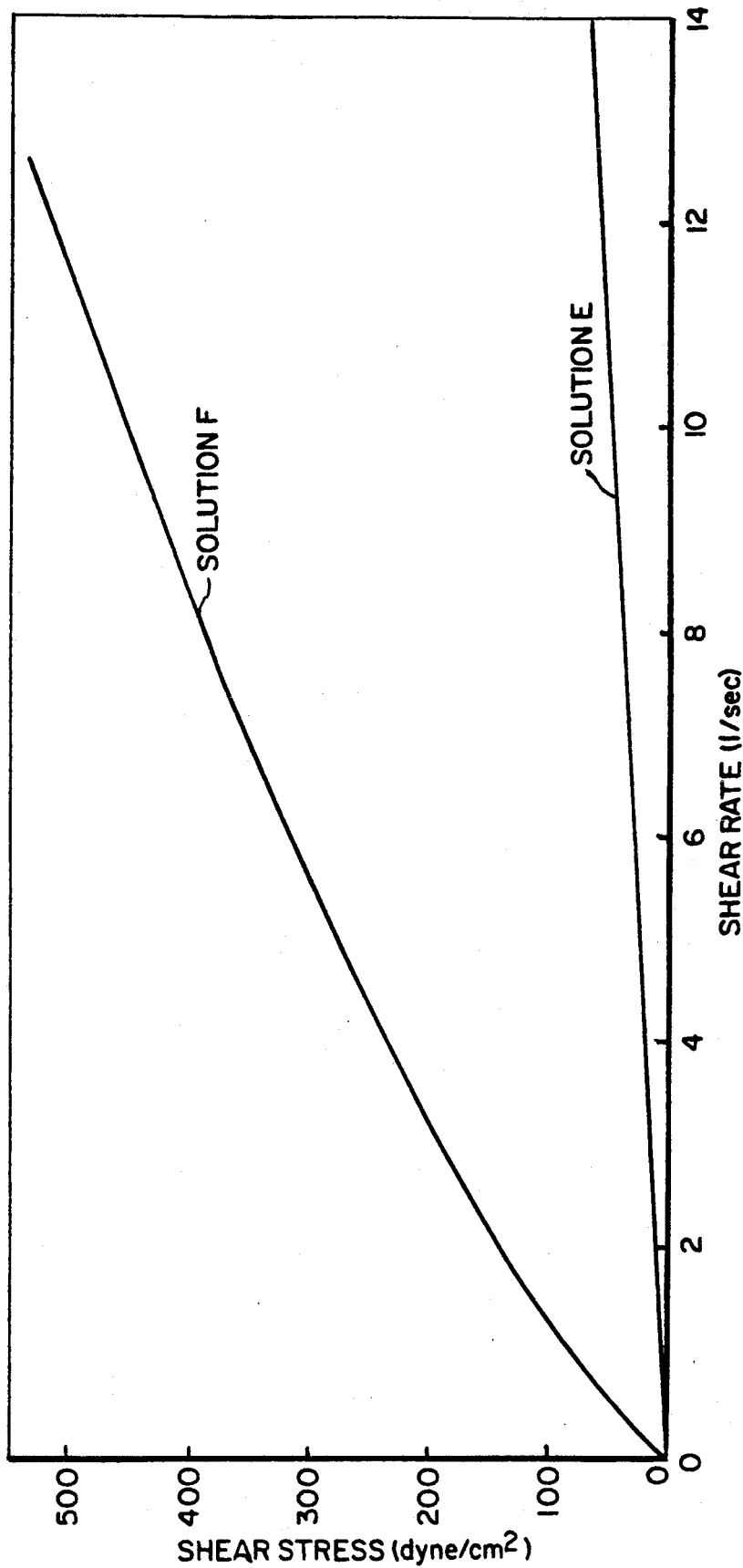
FIG. 3 likewise is presented for comparative purposes and shows viscosity data for solutions containing high molecular weight poly(vinylamine) hydrochloride and the same polymer modified with butyraldehyde.

Solutions E and F were prepared at 3.3 weight percent of modified and unmodified, respectively, polymers in water. Viscosity determinations (Brookfield cylindrical) on the two solutions show a marked decrease in thickening effect for the modified polymer compared to the unmodified polymer. Viscosity of Solution E was 484 cps compared to about 6,000 cps for Solution F. The difference is shown dramatically in FIG. 3 which is a plot of shear stress versus shear rate for the two solutions. It is believed that in this case too much association between the hydrophobic groups took place which is possible because of their short chain length. This result would effectively produce a lower solution viscosity. Consequently, the chain length of the aldehyde hydrophobic modifier should be at least 8 carbons and preferably 10 or more.

Other aspects and embodiments of our invention will be apparent to those skilled in the art from the above disclosure without departing from the spirit or scope of our invention.

We claim:

1. A water-based fluid coating material having sufficient body to be applied to a surface and be retained on that surface while also being sufficiently fluid to form a smooth, coherent film, which coating material contains a thickening amount of a vinylamine polymer which has a weight average molecular weight above $10^5$ and has been modified by reaction with at least 0.2 mer percent of a linear monoaldehyde having 8 to 30 carbon atoms.

2. The coating material of claim 1 wherein said modified polymer contains 0.5 to 20 mols of said monoaldehyde per 100 mols of polymerized monomer units.

3. The coating material of claim 1 wherein said vinylamine polymer is poly(vinylamine).HCl formed by hydrolysis of a homopolymer of N-vinylamide.

4. The coating material of claim 3 wherein said N-vinylamide is N-vinylformamide.

5. The coating material of claim 1 wherein said vinylamine polymer is a copolymer of vinyl alcohol and vinylamine formed by hydrolysis of a copolymer of vinyl acetate and N-vinylamide.

6. The coating material of claim 3 wherein said monoaldehyde is dodecaldehyde reacted in a ratio of 0.5 to 5 mols per 100 mols of vinylamine groups in the polymer chain used to make said polymer.

* * * * *